United States Patent [19]

Isaac et al.

[11] Patent Number: 4,786,497

[45] Date of Patent: Nov. 22, 1988

[54] PROCESS FOR PRODUCING STORABLE CAMOMILE EXTRACTS RICH IN ACTIVE SUBSTANCES

[75] Inventors: Otto Isaac, Hanau; Reinhold Carle, Rodermark, both of Fed. Rep. of Germany

[73] Assignee: Degussa Aktiengesellschaft, Frankfurt am Main, Fed. Rep. of Germany

[21] Appl. No.: 96,211

[22] Filed: Sep. 8, 1987

Related U.S. Application Data

[63] Continuation of Ser. No. 776,632, Sep. 12, 1985, abandoned.

[30] Foreign Application Priority Data

Sep. 19, 1984 [DE] Fed. Rep. of Germany ....... 3434342

[51] Int. Cl.⁴ ..................... A61K 35/78; A61K 31/31; A61K 31/045
[52] U.S. Cl. ................................. 424/195.1; 514/456; 514/729
[58] Field of Search ..................... 424/195.1; 514/456, 514/729

[56] References Cited

FOREIGN PATENT DOCUMENTS 0175185 9/1987 European Pat. Off. .
1093951 12/1960 Fed. Rep. of Germany .
2402802 7/1975 Fed. Rep. of Germany .
3423207 1/1985 Fed. Rep. of Germany .

OTHER PUBLICATIONS

Roch, Arch. Pharm. vol. 280:424–442, 1942.
Chem. Abst. 72:82946m, 1970.
Chem. Abst. 70:99566u, 1969.

Primary Examiner—John Rollins
Attorney, Agent, or Firm—Cushman, Darby & Cushman

[57] ABSTRACT

Improved camomile extracts are obtained by extraction of fresh camomile flowers with aqueous lower alkanols and wthout a subsequent heat treatment.

19 Claims, No Drawings

PROCESS FOR PRODUCING STORABLE CAMOMILE EXTRACTS RICH IN ACTIVE SUBSTANCES

This is a continuation of application Ser. No. 776,632, filed Sept. 12, 1985, which was abandoned upon the filing hereof.

BACKGROUND OF THE INVENTION

Fluid camomile extracts may be obtained in various ways, for example by maceration, percolation, repercolation, or chain percolation. One feature common to all these processes is that the starting material used is the camomile drug, i.e. the dried flowerheads. The quality of camomile flowers and camomile extracts depends not only on the bisabolol content, but also on the contents of ethereal oil, chamazulene and flavones.

The camomile flowers lose 75 to 85% of their weight in the drying process. At the same time, however, the flowers also lose active substances to an extent which depends upon the type of drying process used. In the drying of fresh camomile of the bisabolol type under production conditions, a loss of 47a% of essential oil or rather 48% of chamazulene and 46% of $(-)$-$\alpha$-bisabolol can be expected to occur, for example even at relatively low drying temperatures.

Further losses of active substance occur during storage of the camomile drug. For example, after storage of the camomile drug for 1 year, the essential oil content decreased by 43.8%, the chamazulene content of the essential oil decreasing over proportionally by 68.4%.

Another problem is that the active substances present in the camomile are very difficult to extract from the drug. For example, in the production of fluid extracts with 45% alcohol, ony about half the essential oil in the drug passes over into the extract.

The extraction of fresh camomile (i.e. freshly harvested flowerheads) has not yet been carried out because freshly harvested plants or parts thereof undergo numerous enzymatically controlled or microbially induced processes which affect their contents. It is only through removal of the water during drying that the vegetable enzymes are inactivated or rather denatured. There has only been one reported case (Arch. Phar. 280 (1942), pages 437–38) where fresh camomile is extracted with 86% alcohol, although the extract has to be subsequently boiled for 20 minutes to destroy the enzymes. In this case, however, the azulene yield was only 18.4% and, after only 5 months, the extract had lost virtually all the azulene originally present.

In addition, the active substances in known comamile extracts have only a limited storage life. In particular, there is a rapid reduction in the chamazulene content which cannot be prevented even by addition of alkali.

It has now surprisingly been found that the extraction of fresh camomile in accordance with the present invention has advantages over the known extraction of the camomile drug. In particular, it is possible to improve the yield of active substances and also their storage life.

SUMMARY OF THE INVENTION

Unexpectedly it is not necessary in this regard to stabilize the fresh plant extract by heating. Irrespective of any continuing enzymatic activity, heating of the fresh camomile extract must even be avoided if the above-mentioned advantages are to be obtained.

The process consists essentially of extracting fresh camomile flowers or frozen camomile flowers with an aqueous or anhydrous $C_1$–$C_4$ alkanol, having an alkanol content of 40 to 100% and without a subsequent heat treatment. The extraction is usually carried out at 10° to 60° C. There can be added fresh, frozen, or dried camomile flower petals before or during the extraction.

The product in one form of the invention using flowers of the variety Degumill contains for example at least 18 mg % $(-)$-$\alpha$-bisabolol and less than 9 mg % of other bisaboloids.

The saturation of the fresh camomile flowers is carried out with saturated aliphatic $C_1$–$C_4$ alcohols, such as for example methanol, ethanol, 1-propanol, 2-propanol, 1-butanol, 2-butanol, more especially ethanol and isopropanol. It is possible to use the pure (100%) alcohols or mixtures of these alcohols with water which may have alcohol contents of from 40 to 100% by weight, preferably from 50 to 90% by weight and more preferably from 55 to 85% by weight.

The extraction may be carried out, for example, at a temperature in the range from 10 to 60° C. and preferably at a temperature in the range from 10° to 40° C.

The concentration of alcohol in the extractant depends upon the drug equivalent or upon the dry weight of the camomile which is present in the resulting extract. The drug equivalent of a fresh camomile is the quantity by weight of camomile drug which is obtained from the fresh camomile by drying in the usual way, i.e. by any of the methods normally used in the production of camomile drugs, for example by drying in thin layers away from direct sunlight at temperatures in the range from 40° to 60° C. A drug obtained in this way generally still contains up to 10% by weight of water. By contrast, the dry weight of a camomile is the weight of the substantially anhydrous drug. If, for example, the ratio of fresh camomile to extractant is high, the alcohol content of the extractant has to be relatively high. However, one part by weight of the dry weight of the fresh camomile (as determined by drying a sample in a drying cabinet for 3 hours at 150° C.) should correspond to at least 4 parts by weight, preferably to between 4 and 8 parts by weight and more preferably to between 5 and 6 parts by weight of extract, the alcohol content of the extractant having to be gauged in such a way that the extract never contains any less than 20 percent by weight alcohol. In general, the alcohol content of the extract should amount to between 20 and 50% or 20 and 40% by weight, preferably to between 20 and 35% by weight. 100 g of fresh camomile generally corresponds to a dry weight of from 20 to 30 g. Depending on the alcohol content of the extract, the following fresh camomile (the dry weight of the fresh camomile being, for example, 24.6 g corresponding to a water content of 73.6% by weight): 57 g of ethanol (96% by volume) to 100 g of fresh camomile produce an alcohol content of, for example 40% by weigbht in the extract.

As in the extraction of the drug, the yield of active substances depends upon the alcohol content of the extraction medium. The water bound to the fresh camomile (=water content) together with the alcohol added represents the extraction medium. Taking the water content of the fresh camomile into account, therefore, the addition of alcohol should be so selected as to give the desired alcohol content in the extract. In the context of the invention, fresh camomile flowers (fresh camomile) are understood to be camomile flowers which are extracted or frozed within a period of 24 hours after picking. During this 24 hour period, moderate drying of only at most 10% (based on the water content of the fresh camomile flowers) takes place, according to the weather conditions (temperature, air humidity) prevailing outside.

In general, the camomile flowers are extracted in the first 24 hours after picking. If extraction cannot be carried out in that time, the camomile may be frozen pending extraction.

Frozen camomile flowers may also be used for the process according to the invention, providing fresh camomile flowers (as defined above) are used for freezing. The freezing of the fresh camomile flowers may be carried out, for example, as follows: the fresh camomile is frozen, for example, with cold air at $-10°$ to $-50°$ C., preferably at $-30$ to $-50°$ C. and more preferably at $-35°$ to $-45°$ C. or with liquid gases either continuously or in batches and is stored at temperatures of, for example, from $-10°$ to $-50°$ C., preferably at temperatures of from $-30°$ to $-50°$ and more preferably at temperatures of from $-35°$ to $-45°$ C.

Continuous deep-freezing with liquid gases may be carried out, for example, with carbon dioxide, nitrogen or Freons, preferably with liquid nitrogen, in a tunnel froster. The frozen material is stored at the temperatures indicated above. The deep-frozen camomile flowers may be used for extraction either as such or after careful complete or partial thawing (for example by pouring over the extractant heated to $30°-60°$ C.).

If fresh camomile is extracted instead of the camomile drug, a better yield of active substances is obtained. Thus, on the basis of the same dry weight and the same drug equivalent (1 part of dry weight=5 parts of extract) and an ethanol content of approximately 33% in the extract, the following yields of active substances were obtained, based on the fresh camomile content (=100%) and expressed as dry weight:

|  | Extraction of Fresh camomile | Extraction of camomile drug |
|---|---|---|
| Essential oil | 54.6% | 39.5% |
| Chamazulene | 100% | 24.1% |
| (−)-α-bisabolol | 58.8% | 26.7% |

For this comparison, the drying of the fresh camomile was carried out under mild conditions. However, these mild conditions cannot be reproduced in practice. Accordingly, in a comparison with a drug obtained under normal production conditions, the extraction of fresh camomile in accordance with the invention would emerge as even more efficient.

Accordingly, in the extraction of fresh camomile, not only are there no losses of active substances caused by the drying of the camomile flowers, the extraction yield, particularly of chamazulene and (−)-α-bisabolol, is also improved. In addition, the higher yield of active substances enables a camomile righer in herbage to be used. Accordingly, there is no longer any need to sift out the herbage inevitably accumulating during picking of the flowers.

The extraction of fresh camomile not only eliminates the need to use expensive drying installations but the considerably energy costs involved in the operation of such installations are also eliminated. The costs involved in producing the extract can be significantly reduced in this way.

Tests have shown that, in the extraction of fresh camomile, it is possible to obtain camomile extracts rich in active substances with a lower alcohol content (for example with an alcohol content of 25%) than the content of 45% recommended in the literature. Surprisingly, it has been found that, even in fresh camomile extracts containing 25% of alcohol, the active substances do not undergo any enzymatic changes. By reducing the alcohol content to 25%, the extract obtained has an approximate 20% higher total content of extractive components (water-soluble and water-insoluble) than a camomile drug extract containing 45% of alcohol.

Finally, it has been found that quite unexpectedly that the storage life of the active substances in the fresh camomile extracts is considerably better than in camomile drug extracts. For example, in fresh camomile extracts containing 26% and 40% of ethanol, no reduction in matricin or chamazulene was observed after storage for 9 months at room temperature. Behavior such as this was all the more unexpected insofar as it had been assumed from the nature of the extraction that there would be increased degradation through enzymatic activity. It is known from the literature that chamazulene in particular, which is present in the camomile itself and in the camomile extracts in the form of the preliminary stage matricin, undergoes rapid degradation during storage. Hitherto, there has been no known process capable of permanently ensuring the stability of the matricin in camomile extracts.

TABLE 1

| Content of Active substances in camomile extracts after 9 months (starting value = 100) | | |
|---|---|---|
|  | Extraction of camomile drug | Extraction of fresh camomile |
| Alcohol in the extract | 40% | 40% | 25% |
| Essential oil | 86% | 91% | 86% |
| Chamazulene | 27% | 130% | 109% |
| (−)-α-bisabolol | 98% | 102% | 83% |

As can be seen from Table 1, the azulene content in the extract produced from camomile drug drastically decreases as expected after storage for 9 months, where as the content of essential oil and bisabolol remains relatively stable. In the fresh camomile extracts, the content of essential oil and bisabolol behaves comparably with the drug extract. By contrast, the chamazulene content has remained surprisingly stable and even shows a slight increase over the starting value.

As of the known extraction processes may be used for the extraction of fresh camomile. However, since fresh camomile is more voluminous than the camomile drug, it is best to use the process of maceration or stirred maceration as described, for example, in DE-PS No. 1 093 951.

The process according to the invention may be applied generally to camomiles of any variety. Particularly suitable varieties are the Degumill variety (DDR Degumill "Variety" patent; German Pat. No. 2,402,802; Italian Pat. No. 1,035,096), the Manzana variety (DE-OS No. 34 23 207) and the camomiles according to the German patent application No. 3446216.3.

Thus, fresh camomile extracts according to the invention of camomile flowers of the Degumill variety contain, for example, at least 18 mg of (−)-α-bisabolol and less than 9 mg % of other bisaboloids (such as bisabolol oxides).

Where camomile flowers of the Manzana variety or the camomile flowers according to German patent application P 3446216.3 are used, the camomile extracts according to the invention contain, for example, at least 24 mg % of (—)-α-bisabolol and less than 12 mg % of other bisaboloids.

Since fresh camomile flowers generally contain the associated wing petals either completely or at least in part, the extracts according to the invention also have a higher flavone content than the extracts hitherto produced from dried flowers. It is of course also possible to introduce fresh camomile wing petals, frozen camomile wing petals or even dried camomile wing petals during the extraction according to the invention, so that the flavone content may be additionally increased. The camomile wing petals have a high content of flavones (such as for example apigenin and glycosides thereof).

The process can consist of, or consist essentially of the recited steps with the stated materials.

DETAILED DESCRIPTION

EXAMPLE 1

A quantity of fresh camomile equivalent to 200 g of camomile drug (758 g, water content 73.6%; essential oil 876 mg %; azulene 57 mg %, bisabolol 151 mg %) is extracted with 510 g of ethanol (84% by weight) in a trough mixer at a rotational speed of the mixer of 65 r.p.m. After 30 minutes, the extracted material is pressed and the extract filtered. The content of active substances in the extract is determined in known manner:

| | |
|---|---|
| Azulene | 14.7 mg % |
| Essential oil | 105.7 mg % |
| Bisabolol | 20.4 mg % |
| Apigenin and apigenin glucosides (calculated as apigenin) | 73.1 mg % |
| Extractive components | 5.9% |
| Ethanol | 39.6% (g/g) |

COMPARISON EXAMPLE (known process)

200 g of the camomile flowers used in the preceding Example, but dried for this Example (drying is carried out in a thin layer away from direct sunlight at temperatures below 40° C.; essential oil 598 mg %; azulene 22.7 mg %; bisabolol 150 mg %; water content 9%) are extracted with 1050 g of ethanol (40% by weight) in a trough mixer at a rotational speed of the mixer of 65 r.p.m. After 30 minutes, the drug material is pressed and the extract filtered. The content of active substances in the extract is determined in known manner:

| | |
|---|---|
| Azulene | 4.7 mg % |
| Essential oil | 87.0 mg % |
| Bisabolol | 12.9 mg % |
| Apigenin and apigenin glucosides (calculated as apigenin) | 59.9 mg % |
| Extractive components | 5.3 mg % |
| Ethanol | 37.9% (g/g) |

EXAMPLE 2

A quantity of fresh camomile equivalent to 200 g of camomile drug (952 g; water content 79%; essential oil 876 mg %; azulene 57 mg %, bisabolol 151 mg %) is extracted with 540 g of ethanol (80% by weight) in a trough mixer at a rotational speed of the mixer of 65 r.p.m. After 30 minutes, the extraction material is pressed and the extract is filtered. The content of active substances in the extract is determined in known manner:

| | |
|---|---|
| Azulene | 8.2 mg % |
| Essential oil | 75.5 mg % |
| Bisabolol | 9.1 mg % |
| Apigenin and apigenin glucosides (calculated as apigenin) | 62.2 mg % |
| Extractive components | 6.6 mg % |
| Ethanol | 26.5 (g/g) |

COMPARISON EXAMPLE (known process)

200 g of the camomile flowers used in the previous Example, but dried for this Example (drying as in Comparison Example 1; essential oil 598 mg %; azulene 22.7 mg %; bisabolol 150 mg %; water content 9%) are extracted with 1050 g of ethanol (25% by weight) in a trough mixer at a rotational speed of the mixer of 65 r.p.m. After 30 minutes, the drug material is pressed and the extract is filtered. The content of active substances in the extract is determined in known manner:

| | |
|---|---|
| Azulene | 3.6 mg % |
| Essential oil | 66.0 mg % |
| Bisabolol | 6.7 mg % |
| Apigenin and apigenin glucosides (calculated as apigenin) | 48.9 mg % |
| Extractive components | 6.3 mg % |
| Ethanol | 25.4% (g/g) |

EXAMPLE 3

A quantity of fresh camomile equivalent to 300 g of camomile drug (1154 g; water content 74%; essential oil 950 mg %; azulene 92 mg %; bisabolol oxide A 180 mg %) is extracted with 1330 g of 2-propanol (52% by weight) in a trough mixer at 65 r.p.m. After 90 minutes, the extraction material is pressed and the extract is filtered. The content of active substances in the extract is determined in known manner:

| | |
|---|---|
| Azulene | 14.2 mg % |
| Essential oil | 101.5 mg % |
| Bisabolol oxide A | 26.0 mg % |
| Apigenin and apigenin glucosides (calculated as apigenin) | 57.0 mg % |
| Extractive components | 6.9 mg % |
| 2-propanol | 26.0% (g/g) |

COMPARISON EXAMPLE (known process)

300 g of the camomile flowers used in the previous Example, but dried for this Example (drying as in Comparison Example 1; essential oil 740 mg %; azulene 56 mg %; bisabolol oxide A 168 mg %; water content 9%) are extracted with 2100 g of 2-propanol (33% by weight) in a trough mixer at a mixer speed of 65 r.p.m. After 90 minutes, the drug material is pressed and the extract is filtered. The content of active substances in the extract is determined in known manner:

| | | |
|---|---|---|
| Azulene | 6.7 | mg % |
| Essential oil | 85.2 | mg % |
| Bisabolol oxide A | 17.4 | mg % |
| Apigenin and apigenin glucosides (calculated as apigenin) | 52.4 | mg % |
| Extractive components | 6.6 | mg % |
| 2-propanol | 28.5% | (g/g) |

What is claimed is:

1. A process for producing a storable camomile extract rich in active substances including a bisabloid consisting essentially of extracting fresh camomile flowers or frozen camomile flowers with an aqueous or anhydrous $C_1$-$C_4$ alkanol having an alkanol content of 40 to 100% and with the absence of subsequent heat treatment, the amount of alkanol being such that the amount of camomile extract produced is at least 4 parts for each part of camomile flowers used, based on the dried weight of the camomile flowers.

2. A process according to claim wherein there are employed fresh camomile flowers.

3. A process according to claim 1 consisting of extracting the fresh camomile flowers or frozen camomile flowers with the aqueous or anhydrous $C_1$-$C_4$ alkanol.

4. A process according to claim 1 wherein at no time are the camomile flowers subjected to a temperature above 60° C.

5. A process according to claim 4 wherein at no time are the flowers subjected to a temperature above 40° C.

6. A process according to claim 1 wherein the extraction is carried out at a temperature in the range of 10° to 60° C.

7. A process according to claim 6 wherein there are employed fresh camomile flowers.

8. A process according to claim 6 including the step of additionally introducing fresh, frozen, or dried camomile flower petals before or during the extraction.

9. A process according to claim 1 including the step of additionally introducing fresh, frozen, or dried camomile wing petals before or during the extraction.

10. A storable camomile extract rich in active substances obtainable by the process of claim 1.

11. A storable camomile extract according to claim 10 wherein there are employed fresh camomile flowers.

12. A storable camomile extract according to claim 11 containing 20 to 50% of the alkanol by weight.

13. A storable camomile extract according to claim 12 containing 20 to 35% of the alkanol by weight.

14. A storable camomile extract according to claim 12 wherein the alkanol is ethanol or isopropanol.

15. A storable camomile extract according to claim 10 containing 20 to 50% of the alkanol by weight.

16. A storable camomile extract according to claim 15 wherein the alkanol is ethanol or isopropanol.

17. A storable camomile extract according to claim 10 containing in the active substances at least 18 mg % (—)-α-bisabolol and less than 9 mg % of other bisabolids.

18. A storable camomile extract according to claim 17 wherein there are employed fresh or frozen camomile flowers.

19. A storable camomile extract rich in active substances obtainable by the process of claim 8.

* * * * *